United States Patent
Nagata

(10) Patent No.: US 11,037,672 B2
(45) Date of Patent: Jun. 15, 2021

(54) MEDICAL IMAGE PROCESSING APPARATUS, MEDICAL IMAGE PROCESSING METHOD, AND SYSTEM

(71) Applicant: ZIOSOFT, INC., Tokyo (JP)

(72) Inventor: Tsuyoshi Nagata, Tokyo (JP)

(73) Assignee: ZIOSOFT, INC., Tokyo (JP)

( * ) Notice: Subject to any disclaimer, the term of this patent is extended or adjusted under 35 U.S.C. 154(b) by 0 days.

(21) Appl. No.: 16/775,418

(22) Filed: Jan. 29, 2020

(65) Prior Publication Data

US 2020/0243184 A1 Jul. 30, 2020

(30) Foreign Application Priority Data

Jan. 29, 2019 (JP) .............................. JP2019-013563

(51) Int. Cl.
*G16H 30/40* (2018.01)
*G06T 15/00* (2011.01)
*G06T 15/06* (2011.01)
*G06T 15/08* (2011.01)
*G06T 17/20* (2006.01)

(52) U.S. Cl.
CPC ........... *G16H 30/40* (2018.01); *G06T 15/005* (2013.01); *G06T 15/06* (2013.01); *G06T 15/08* (2013.01); *G06T 17/20* (2013.01); *G06T 2210/41* (2013.01)

(58) Field of Classification Search
None
See application file for complete search history.

(56) References Cited

U.S. PATENT DOCUMENTS

| | | |
|---|---|---|
| 2006/0103670 A1 | 5/2006 | Matsumoto |
| 2008/0008368 A1* | 1/2008 | Matsumoto ............. G06T 19/00 382/128 |
| 2008/0297509 A1 | 12/2008 | Matsumoto |
| 2012/0093278 A1* | 4/2012 | Tsukagoshi ........... G06T 11/008 378/4 |
| 2012/0313943 A1* | 12/2012 | Tsukagoshi .............. A61B 8/13 345/424 |

FOREIGN PATENT DOCUMENTS

| | | |
|---|---|---|
| JP | 2008-289767 A | 12/2008 |
| JP | 4188900 B2 | 12/2008 |

* cited by examiner

*Primary Examiner* — Michelle Chin
(74) *Attorney, Agent, or Firm* — Pearne & Gordon LLP

(57) ABSTRACT

A medical image processing apparatus for visualizing a tissue includes: a memory; and a processor configured to execute a process. The process includes: acquiring volume data including the tissue; setting a cut surface for cutting the tissue in the volume data; and first performing processing relating to visualization of the tissue. The first performing includes: second performing rendering that causes ray attenuation on the volume data to generate a rendering image including the tissue cut along the cut surface; and displaying on a display unit display information including the rendering image in which a contour line of the tissue on the cut surface is highlighted.

12 Claims, 17 Drawing Sheets

MEDICAL IMAGE PROCESSING APPARATUS, MEDICAL IMAGE PROCESSING METHOD, AND SYSTEM

CROSS-REFERENCE TO RELATED APPLICATIONS

This application is based on and claims priority under 35 USC 119 from Japanese Patent Application No. 2019-013563 filed on Jan. 29, 2019, the contents of which are incorporated herein by reference.

TECHNICAL FIELD

The present disclosure relates to a medical image processing apparatus, a medical image processing method, and a system.

BACKGROUND

In organ resection and excision, a tubular tissue containing blood vessels is ligated and separated. It is preferable to perform pre-operative planning before surgery the tubular tissue to be ligated and separated. An image display method for visualizing tubular tissue is known in the related art. The image display method displays an image with respect to a tubular tissue through three-dimensional image processing of a region obtained by performing cutting at a cut surface along a path representing a center line of the tubular tissue and through two-dimensional image processing with respect to the cut surface. The three-dimensional image processing is image processing performed through a ray-casting method. The two-dimensional image processing is image processing performed through an MPR method.

It is possible to visualize a cut surface of a tissue with technique of U.S. Patent Application Publication No. 2008/0297509. However, in a case where an image is generated by volume rendering through a ray-casting method, in some cases, it is difficult to grasp the position of a tubular tissue (for example, a blood vessel) in the image. It is more difficult to grasp where the cut surface exists in the tubular tissue in the image. Accordingly, it is difficult to visually recognize a tissue to be ligated in the image.

The present disclosure has been made in consideration of the above-described circumstances and provides a medical image processing apparatus which can easily visually recognize a tissue to be ligated, a medical image processing method, and a system.

SUMMARY

One aspect of the present disclosure provides a medical image processing apparatus for visualizing a tissue that includes: a memory; and a processor configured to execute a process. The process includes: acquiring volume data including the tissue; setting a cut surface for cutting the tissue in the volume data; and first performing processing relating to visualization of the tissue. The first performing includes: second performing rendering that causes ray attenuation on the volume data to generate a rendering image including the tissue cut along the cut surface; and displaying on a display unit display information including the rendering image in which a contour line of the tissue on the cut surface is highlighted.

According to the present disclosure, it is possible to easily visually recognize a tissue to be ligated.

DESCRIPTION OF EMBODIMENTS

Hereinafter, an embodiment of the present disclosure will be described with reference to the drawings.

A medical image processing apparatus for visualizing a tissue, which relates to the embodiment, includes: a memory; and a processor configured to execute a process. The process includes: acquiring volume data including the tissue; setting a cut surface for cutting the tissue in the volume data; and first performing processing relating to visualization of the tissue. The first performing includes: second performing rendering that causes ray attenuation on the volume data to generate a rendering image including the tissue cut along the cut surface; and displaying on a display unit display information including the rendering image in which a contour line of the tissue on the cut surface is highlighted.

Accordingly, in the medical image processing apparatus, it is possible to easily identify where the cut surface in the tissue is by checking highlighted rendering image. Namely, it is possible to easily visually recognize a tissue to be ligated.

Circumstances on How Aspect of Present Disclosure is Obtained

Figure 3A:
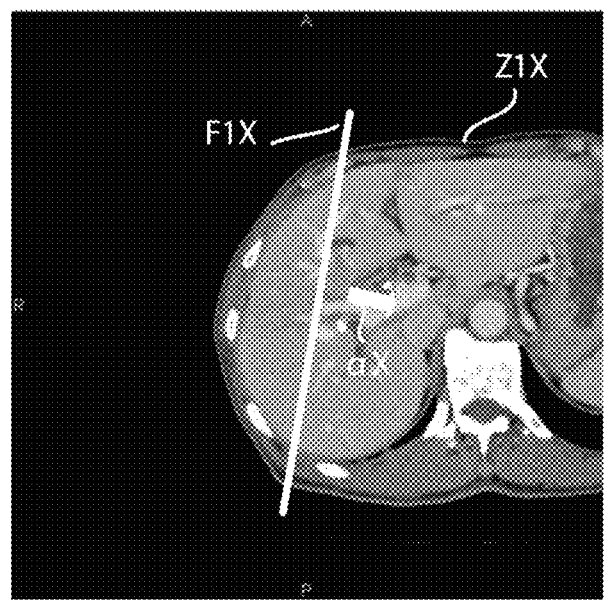
FIG. 3A is a diagram illustrating a ligation and separation point in a raycast image in the related art.
Figure 3B:
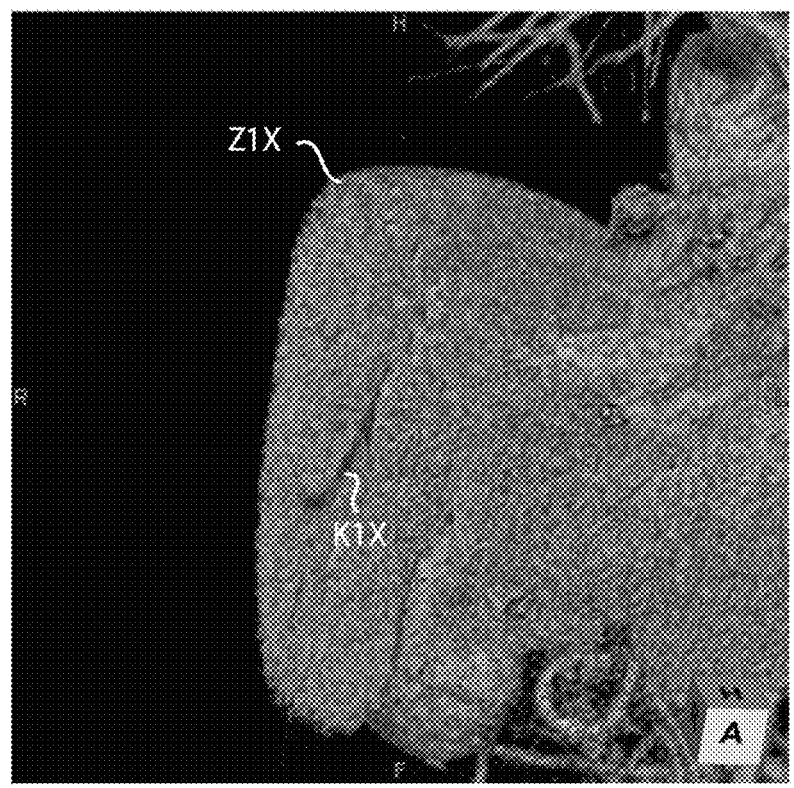
FIG. 3B is a diagram illustrating a ligation and separation point in a raycast image in the related art.

FIGS. 3A and 3B are diagrams illustrating a ligation and separation point in a raycast image in the related art. In ligation and separation, for example, an organ is cut except for blood vessels. The blood vessels are ligated and cut in the state of being ligated. FIG. 3A is a diagram illustrating a cut surface F1X obtained by partially excising an organ Z1X. FIG. 3B is a diagram illustrating a raycast image of the organ Z1X which has been generated based on each voxel positioned in an arrow αX direction than the cut surface F1X. Accordingly, the interior of the organ Z1X is shown in FIG. 3B. However, in many cases, a shading of the raycast image becomes unclear, and in FIG. 3B, the boundary between the surface of the organ Z1X and the cut surface F1X is unclear. For example, it is difficult to distinguish whether a blood vessel K1X included in the raycast image of FIG. 3B is a blood vessel to be ligated and separated or a blood vessel that does not require ligation and separation since the blood vessel is folded back to the back side of the organ Z1X. Voxel values in a case where there is noise or calcification in the image become relatively large. Therefore, it is difficult to distinguish noise or calcification from blood vessels in the image. Blood vessels may be ligated after an organ is partially cut away while leaving the blood vessels intact.

Figure 4A:
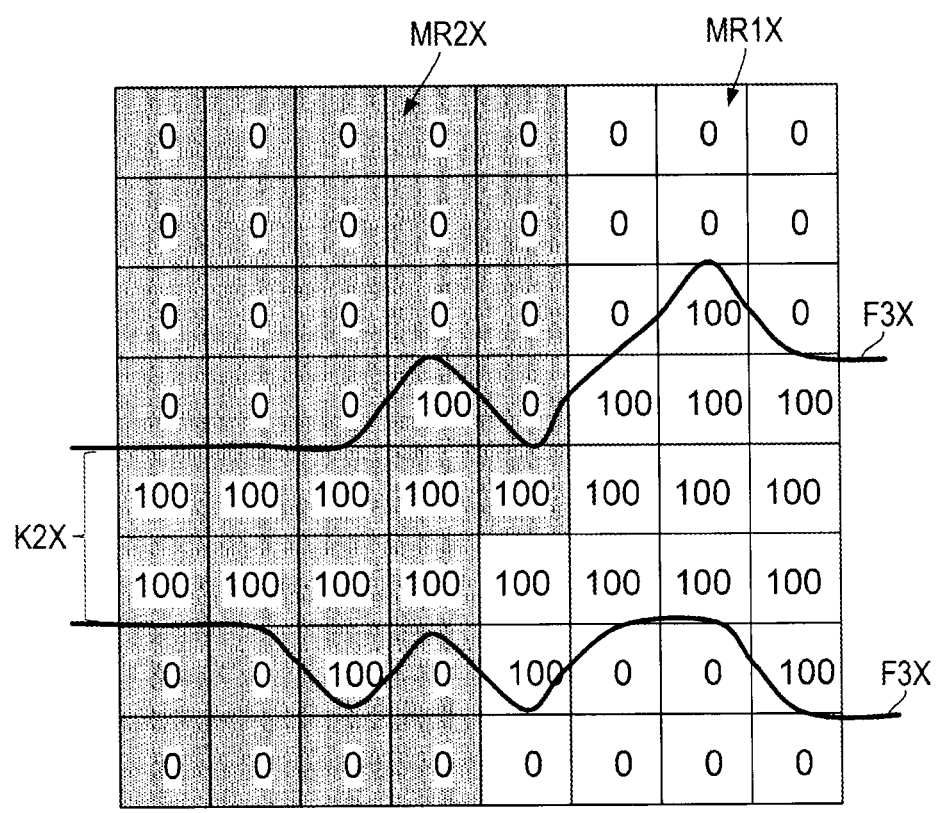
FIG. 4A is a diagram representing a first example of a cross section in the vicinity of a blood vessel in the related art.

FIG. 4A represents a first example of a cross section in the vicinity of a blood vessel in the related art. In FIG. 4A, a blood vessel K2X is planarly represented, but is actually represented by voxels in a three-dimensional space (the same applies to FIG. 4B). The region positioned on the right side in FIG. 4A is a mask region MR1X. The region positioned on the left side in FIG. 4A is a non-mask region MR2X. The numerical values (for example, "0" or "100") illustrated in FIG. 4A represent voxel values. In FIG. 4A, the voxel value of a blood vessel portion is 100 and the voxel value of an organ portion that is not a blood vessel is 0. The non-mask region MR2X represents an excision region and the mask region MR1X represents a residual region.

In a case where voxels having a voxel value greater than or equal to 50 are volume rendered (for example, ray-casted) without using a mask while setting the visual line direction (for example, a direction from the front left side of the paper of FIG. 4A toward the back right side) as a projection direction of a virtual ray, a contour surface F3X is visualized and the blood vessel K2X is drawn. That is, the entire blood vessel K2X shown in FIG. 4A is visualized. In this case, it is unclear which part of the blood vessel is to be excised.

Figure 4B:
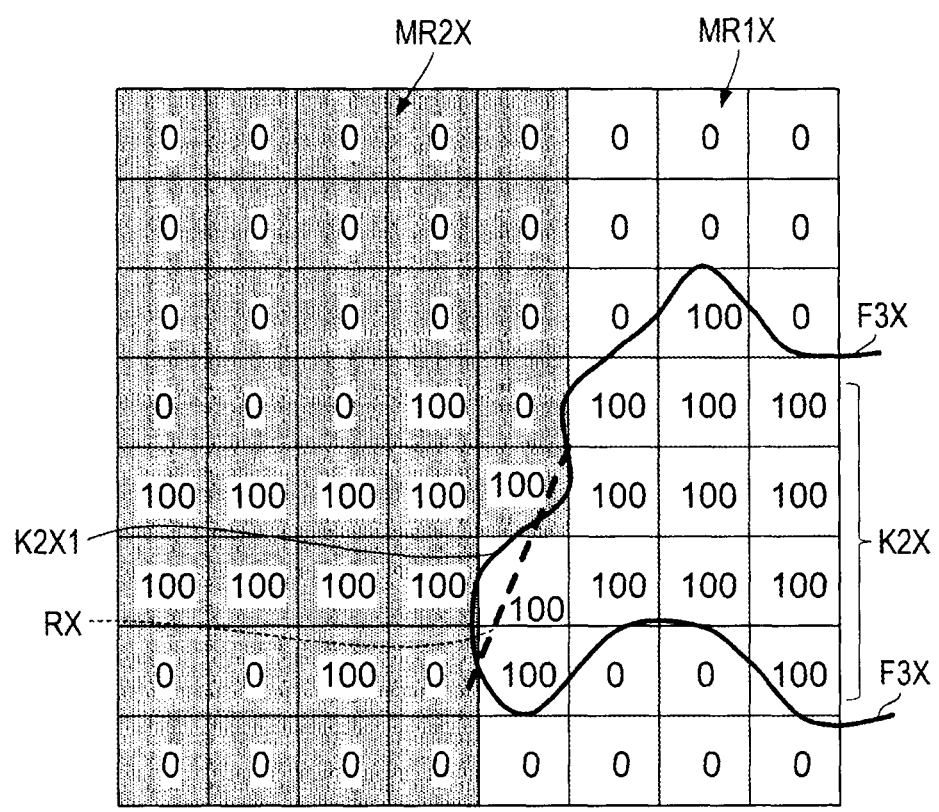
FIG. 4B is a diagram representing a second example of a cross section in the vicinity of a blood vessel in the related art.

FIG. 4B represents a second example of a cross section in the vicinity of a blood vessel in the related art. In a case where voxels having a voxel value greater than or equal to 50 are volume rendered (for example, ray-casted) using a mask while setting the visual line direction (for example, a direction from the front left side of the paper of FIG. 4B toward the back right side) as a projection direction of a virtual ray, the blood vessel K2X within the mask region MR1X is drawn. There is a distal end K2X1 of the blood vessel, to be excised, at the boundary between the mask region MR1X and the non-mask region MR2X. Accordingly, the residual portion of the excised blood vessel K2X is visualized in FIG. 4B. The distal end K2X1 of the blood vessel is visualized as a part of the blood vessel K2X. For this reason, it is difficult to determine whether the distal end K2X1 of the blood vessel K2X is obtained by visualizing the boundary (mask boundary) between the mask region MR1X and the non-mask region MR2X or is obtained by visualizing the contour surface F3X of the voxel values. It is also difficult to determine whether the actual point to be subjected to ligation and separation is a position RX or the blood vessel K2X.

A medical image processing apparatus which can easily visually recognize a tissue to be ligated, a medical image processing method, and a medical image processing program will be described in the following embodiment.

First Embodiment

Figure 1:
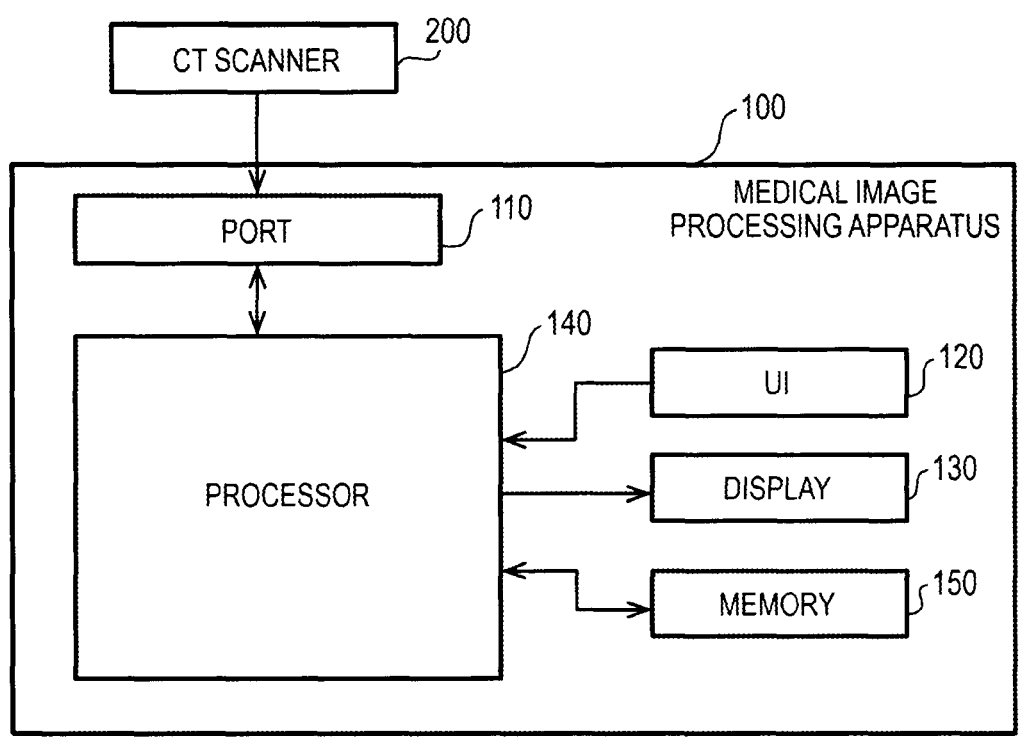
FIG. 1 is a block diagram illustrating a hardware configuration example of a medical image processing apparatus according to a first embodiment.

FIG. 1 is a block diagram illustrating a configuration example of a medical image processing apparatus 100 according to a first embodiment. The medical image processing apparatus 100 includes a port 110, a UI 120, a display 130, a processor 140, and a memory 150.

A CT (Computed Tomography) scanner 200 is connected to the medical image processing apparatus 100. The medical image processing apparatus 100 obtains volume data from the CT scanner 200 and processes the acquired volume data. The medical image processing apparatus 100 may be constituted by a PC and software mounted on the PC.

The CT scanner 200 irradiates a subject with X-rays to capture an image (CT image) using a difference in absorption of X-rays due to tissues in the body. The subject may include a living body, a human body, an animal, and the like. The CT scanner 200 generates volume data including information on any portion inside the subject. The CT scanner 200 transmits the volume data as a CT image to the medical image processing apparatus 100 via a wire circuit or a wireless circuit. When capturing a CT image, imaging conditions relating to CT imaging or contrast conditions relating to administration of a contrast medium may be considered. The imaging may be performed on arteries or veins of an organ. The imaging may be performed a plurality of times at different timings depending on the characteristics of the organ.

The port 110 in the medical image processing apparatus 100 includes a communication port, an external device connection port, or a connection port to an embedded device and acquires volume data obtained from the CT image. The acquired volume data may be immediately sent to the processor 140 for various kinds of processing, or may be sent to the processor 140 as necessary after being stored in the memory 150. The volume data may be acquired via a recording medium or a recording media. The volume data may be acquired in the form of intermediate data, compressed data, or sinogram. The volume data may be acquired from information from a sensor device attached to the medical image processing apparatus 100. The port 110 functions as an acquisition unit that acquires various data such as volume data.

The UI 120 may include a touch panel, a pointing device, a keyboard, or a microphone. The UI 120 receives any input operation from a user of the medical image processing apparatus 100. The user may include a medical doctor, a radiology technician, a student, or other paramedic staffs.

The UI 120 receives various operations. For example, the UI receives operations such as designation of a region of interest (ROI) or setting of luminance conditions in volume data or an image based on the volume data (for example, a three-dimensional image or a two-dimensional image to be described below). The region of interest may include regions of various tissues (for example, blood vessels, the bronchi, organs, bones, and the brain). The tissues may include lesion tissue, normal tissue, tumor tissue, and the like.

The display 130 may include, for example, an LCD, and displays various pieces of information. Various pieces of information may include a three-dimensional image or a two-dimensional image obtained from volume data. The three-dimensional image may include a volume rendering image, a surface rendering image, a virtual endoscopic image, a virtual ultrasound image, a CPR image, and the like. The volume rendering image may include a ray-sum image, an MIP image, a MinIP image, an average value image, or a raycast image. The two-dimensional image may include an axial image, a sagittal image, a coronal image, an MPR image, and the like.

The memory 150 includes various primary storage devices such as ROM or RAM. The memory 150 may include a secondary storage device such as an HDD or an SSD. The memory 150 may include a tertiary storage device such as a USB memory or an SD card. The memory 150 stores various pieces of information and programs. The various pieces of information may include volume data acquired by the port 110, an image generated by the processor 140, setting information set by the processor 140, and various programs. The memory 150 is an example of a non-transitory recording medium in which programs are recorded.

The processor 140 may include a CPU, a DSP, or a GPU. The processor 140 functions as a processing unit 160 performing various kinds of processing and controls by executing a medical image processing program stored in the memory 150.

Figure 2:
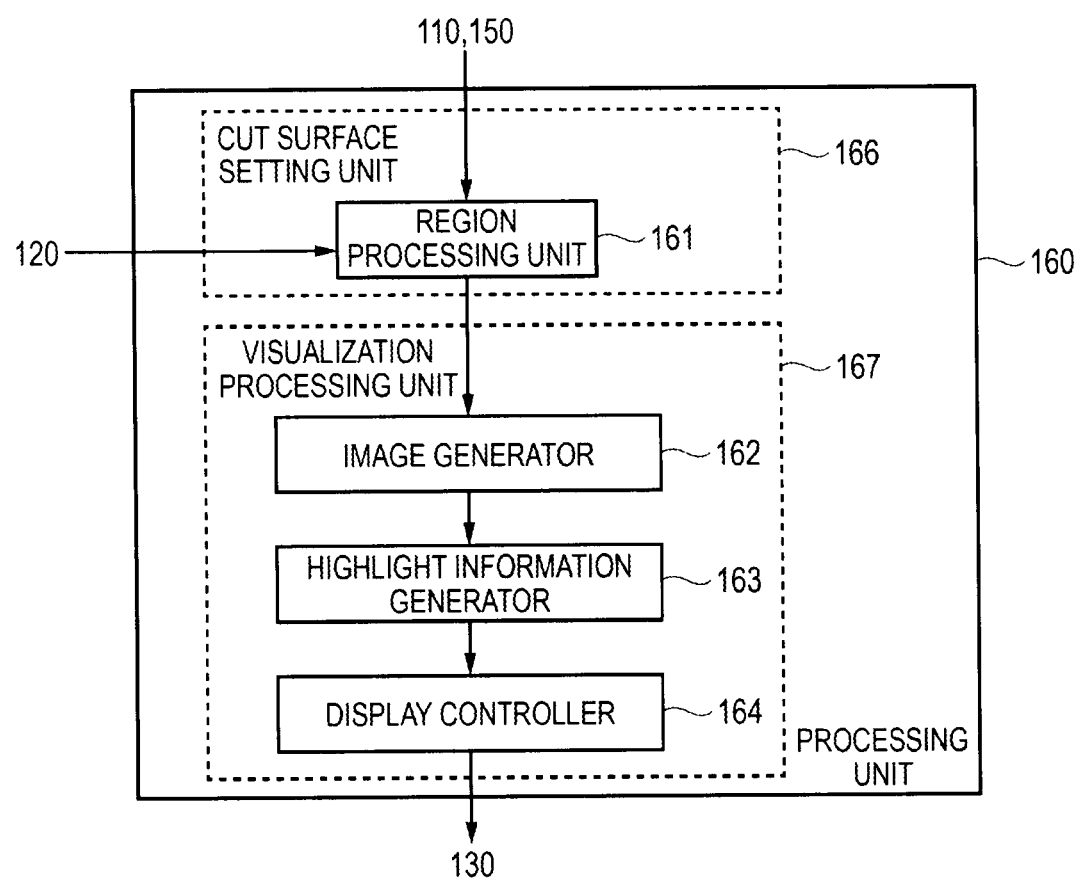
FIG. 2 is a block diagram illustrating a functional configuration example of the medical image processing apparatus.

FIG. 2 is a block diagram illustrating a functional configuration example of the processing unit 160.

The processing unit 160 includes a cut surface setting unit 166 that sets a cut surface for cutting a tissue in volume data and a visualization processing unit 167 that performs processing relating to visualization of the tissue. The cut surface setting unit 166 includes a region processing unit 161. The visualization processing unit 167 includes an image generator 162, a highlight information generator 163, and a display controller 164. The processing unit 160 controls each portion of the medical image processing apparatus 100. The processing unit 160 performs processing relating to visualization of the tissue. Each portion included in the processing unit 160 may be realized as different functions using one hardware device or may be realized as different functions using a plurality of hardware devices. Each portion included in the processing unit 160 may be realized using exclusive hardware components.

The region processing unit 161 acquires volume data of a subject via the port 110, for example. The region processing unit 161 extracts any region contained in the volume data. The region processing unit 161 may extract a region of interest by automatically designating the region of interest based on voxel values of the volume data, for example. The region processing unit 161 may extract a region of interest by manually designating the region of interest via, for example, the UI 120. The region of interest may contain regions of the lung, the liver, the bronchi, the pulmonary arteries, the pulmonary veins, the portal vein, and the hepatic veins. The region of interest may be at least a part of an organ to be excised from a subject.

The region processing unit 161 may segment an organ of a subject. The segments may be roughly coincident with at least anatomical segments. The organ may contain the lung, the liver, and other organs. The segments may be at least some regions out of a combination of a plurality of segments. The segments may include sub-segments, sub-sub-segments, and the like which are units in a finer range than that of the segments.

The region processing unit 161 may set a cut surface for cutting a tissue. In this case, a cut surface may be manually set via the UI 120, or may be automatically set based on operation results. For example, when segmenting the lung, the region processing unit 161 may extract a plurality of segments of the lung to set boundary surfaces between the plurality of segments as cut surfaces. The cut surfaces may be flat or curved. The cut surfaces may be coincident with ligation and separation points (ligation and separation surfaces).

The image generator 162 generates various images. The image generator 162 generates a three-dimensional image or a two-dimensional image based on at least a part of acquired volume data (for example, volume data of extracted regions or segments). The image generator 162 may generate an image by performing rendering (for example, ray-casting or surface rendering) that causes ray attenuation. The image generator 162 may generate an image using a mask. If a mask is used, drawing is performed within an image while being limited to voxels of a mask region, and drawing is not performed within an image with voxels of a non-mask region. A plurality of masks can be used for each region. The generation of an image using a mask is disclosed, for example, in Japanese Patent No. 4188900 which is incorporated herein by reference.

The highlight information generator 163 generates highlight information for highlighting a contour line of a tissue on a cut surface or a cut surface itself of a tissue (the inside surface of the contour line). The highlight information includes at least contour line highlight information in which a contour line of a tissue on a cut surface is highlighted.

The contour line highlight information may be a ring formed substantially along a contour line of a tubular tissue on a cut surface. For example, the contour line highlight information may include information in which voxel values of voxels of a contour line of a tissue on a cut surface are greater than acquired actual values. The contour line highlight information may include information in which a contour line of a tissue on a cut surface is made thick. The contour line highlight information may include information in which voxels of a contour line have a color different from other voxels adjacent to the contour line.

The highlight information may include surface highlight information in which the inside surface of the contour line of a cut surface is highlighted. The surface highlight information may be a shape, a pattern, a color, plotting out, and the like of the inside of a ring indicating the contour line of the cut surface. For example, the surface highlight information may include information in which voxel values of voxels on a cut surface are greater than acquired actual values. The surface highlight information may include information in which the colors of voxels of a cut surface are different from those of other voxels adjacent to the cut surface.

A tissue having a cut surface may be a tissue to be ligated and separated. The tissue may be, for example, tubular tissue. The tubular tissue may include blood vessels, lymphatic vessels, the bronchi, the bile duct, and the like. The ligation and separation may be carried out along with removal of a tumor from an organ, segmentectomy of an organ, wedge-shaped excision of an organ, and the like. The tubular tissue may be a tissue contained in an organ (for example, the lung or the liver). The highlight information may be information in which the direction of the tubular tissue is visualized. The highlight information may be generated based on a path of the tubular tissue. The highlight information may be displayed while being offset from a cut surface.

The display controller 164 displays various data, information, and images on the display 130. The images include images generated in the image generator 162. The display controller 164 displays highlight information so that the highlight information is superimposed on a rendering image.

Figure 5:
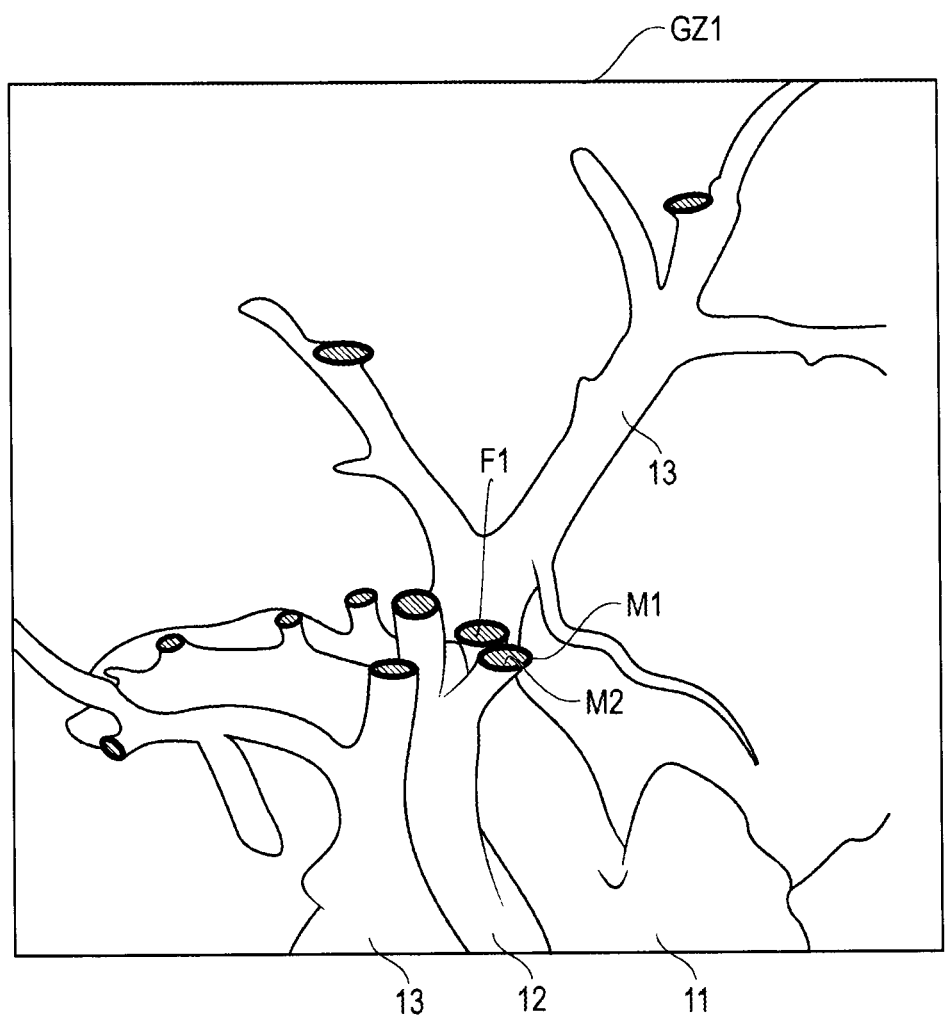
FIG. 5 is a diagram illustrating highlighted ligation and separation points.

FIG. 5 is a diagram illustrating highlighted ligation and separation points. A raycast image GZ1 including a bronchus 11, a pulmonary artery 12, and a pulmonary vein 13 is shown in FIG. 5. In FIG. 5, the bronchus 11, the pulmonary artery 12, and the pulmonary vein 13 have a cut surface F1. The bronchus 11, the pulmonary artery 12, and the pulmonary vein 13 may be visualized through volume rendering (for example, ray-casting). The cut surface F1 may be visualized through surface rendering. The cut surface F1 may be substantially coincide with a ligation and separation point.

The cut surface F1 is highlighted according to highlight information. The highlight information includes at least one of contour line highlight information M1 or surface highlight information M2. The display controller 164 highlights boundaries between voxels, voxels visualized on the cut surface F1 and non-visualized voxels adjacent to the cut surface F1, based on the highlight information. A user easily visually recognizes the boundaries between the voxels pertaining to the cut surface F1 according to the display of a highlighted cut surface F1. The display controller 164 may perform display while distinguishing the voxels visualized on the cut surface F1 from the non-visualized voxels adjacent to the cut surface F1 using different display modes (for example, different colors).

Figure 6A:
FIG. 6A is a diagram illustrating an example of a raycast image including the hepatic veins and the portal vein before excision.
Figure 6B:
FIG. 6B is a diagram illustrating an example of a raycast image displaying non-highlighted cut surfaces of the hepatic veins and the portal vein after excision.
Figure 6C:
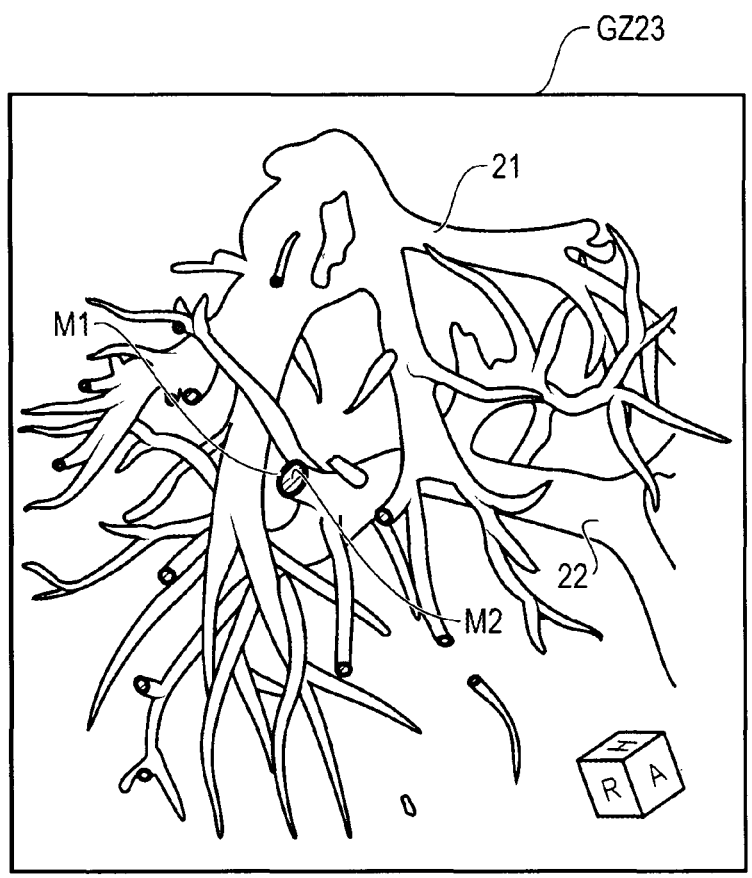
FIG. 6C is a diagram illustrating an example of a raycast image representing highlighted cut surfaces of the hepatic vein and the portal vein after excision.

FIGS. 6A to 6C are diagrams illustrating examples of rendering images after excision. FIG. 6A illustrates a raycast image GZ21 including a hepatic vein 21 and a portal vein 22 before excision. FIG. 6B illustrates a raycast image GZ22 displaying non-highlighted cut surfaces F1 of the hepatic vein 21 and the portal vein 22 after excision. FIG. 6C illustrates a raycast image GZ23 displaying the highlighted cut surfaces F1 of the hepatic vein 21 and the portal vein 22 after excision using highlight information. When comparing FIG. 6B with FIG. 6C, it is possible to understand that blood vessels simply ended (here, the hepatic vein 21 and the portal vein 22) are easily distinguished from blood vessels cut at the cut surfaces F1 using the contour line highlight information M1 and the surface highlight information M2 as highlight information. Accordingly, even in a case of segmenting a portion where the complicatedly intertwined hepatic vein 21 and portal vein 22 exist, it is possible to clearly recognize points to be cut. For example, it is possible to easily visually recognize points at which fine blood vessels are to be ligated during surgery for performing segmentectomy by making cut surfaces coincide with segmentation surfaces of segmentation.

Figure 7A:
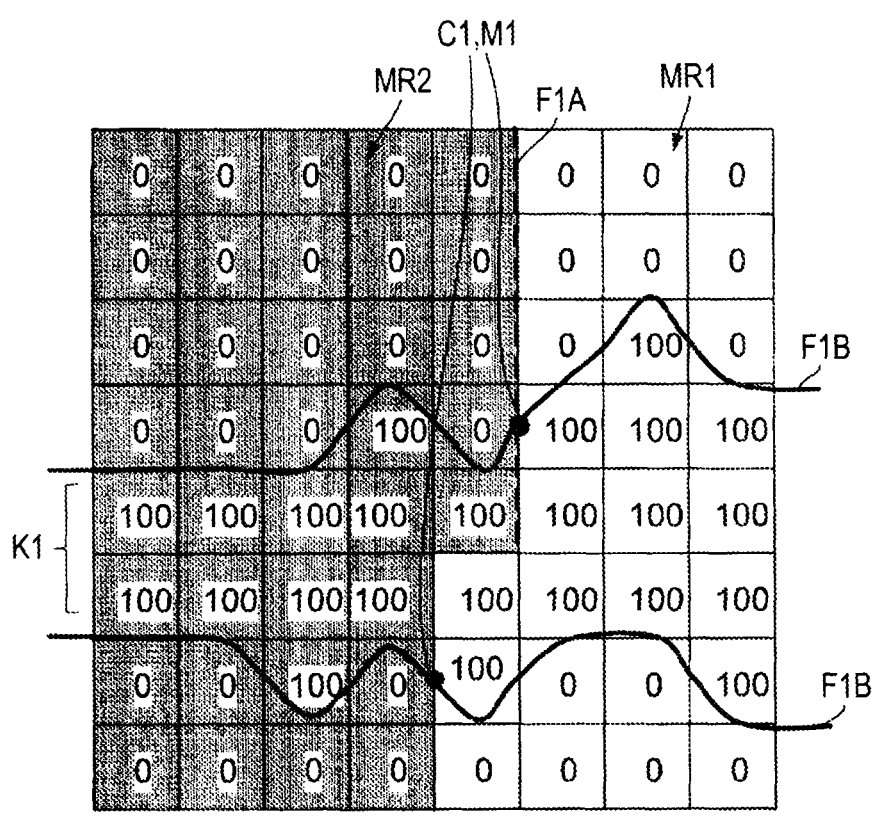
FIG. 7A is a diagram illustrating a first example of display of a highlighted cut surface of a blood vessel and each voxel value in a rendering image.

FIG. 7A is a diagram illustrating a first example of display of the highlighted cut surface F1 of the blood vessel K1 and each voxel value in a rendering image. In FIG. 7A, highlighted display is performed using the contour line highlight information M1. In FIG. 7A, the blood vessel K1 is planarly represented, but is actually represented by voxels in a three-dimensional space (the same applies to FIGS. 7B and 8A). The contour line highlight information M1 is represented by a closed-ring curve in the three-dimensional space. The region positioned on the right side in FIG. 7A is a mask region MR1. The region positioned on the left side in FIG. 7A is a non-mask region MR2. The numerical values (for example, "0" and "100") described in FIG. 7A represent voxel values. In FIG. 7A, a voxel value of a blood vessel portion is 100 and a voxel value of an organ portion which is not a blood vessel is 0.

The highlight information generator 163 calculates an intersection point C1 between a boundary (mask boundary surface F1A) between the mask region MR1 and the non-mask region MR2 and a contour surface F1B indicating boundaries between the voxel values 0 and 100. The intersection points C1 coincide with two points obtained at which the contour line of a tissue (here, the blood vessel K1) on the cut surface F1 is projected onto the plane of FIG. 7A. The contour lines of the tissue are represented by the two intersection points C1 in the plane of FIG. 7A, but are represented by intersection lines between the mask boundary surface F1A and the contour surface F1B on three-dimensional volume data. The intersection lines are cyclic and coincide with contour lines of tissues on set cut surfaces F1. Although the cut surface F1 is set corresponding to the mask boundary surface F1A, the cut surface F1 itself is not visualized in FIG. 7A.

Figure 7B:
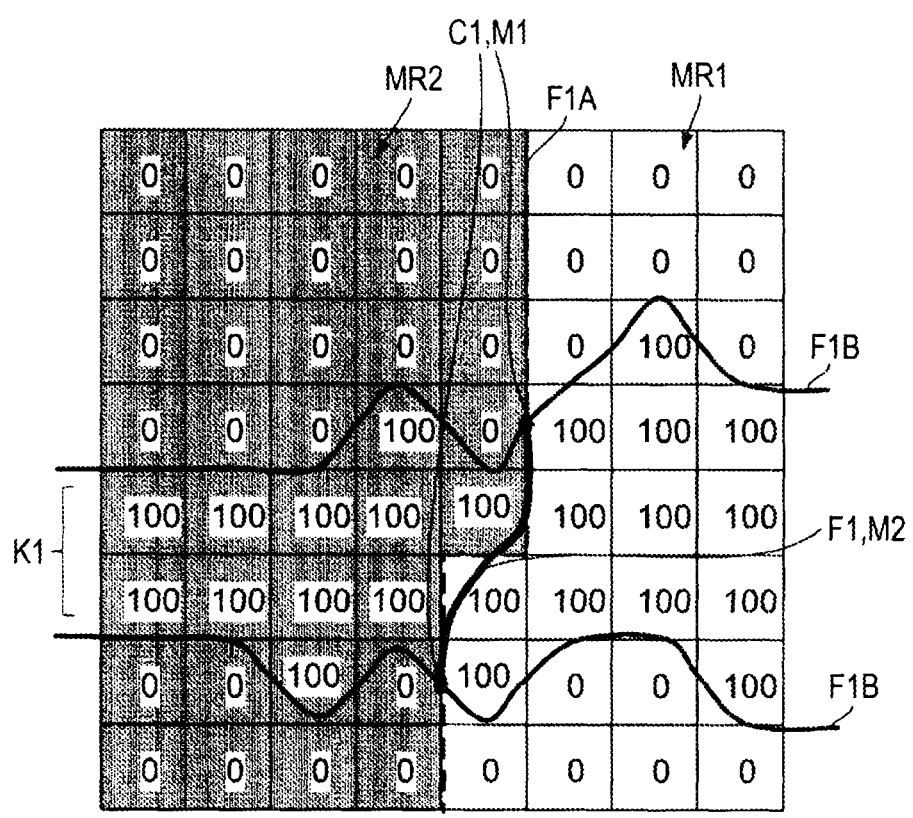
FIG. 7B is a diagram illustrating a second example of display of a highlighted cut surface of a blood vessel and each voxel value in a rendering image.

FIG. 7B is a diagram illustrating a second example of display of a highlighted cut surface F1 of the blood vessel K1 and each voxel value in a rendering image. In FIG. 7B, highlighted display is performed using the contour line highlight information M1 and the surface highlight information M2. The mask region MR1, the non-mask region MR2, and voxel values of voxels are shown in FIG. 7B in the same manner as in FIG. 7A. The surface formed by the intersection points C1 within the closed-ring curve represents the cut surface F1 of the blood vessel K1. The contour line highlight information M1 is represented by a closed-ring curve in the three-dimensional space. The surface highlight information M2 may be flat or curved. The display controller 164 may highlight the surface highlight information M2 along the cut surface F1 in a display mode (for example, different colors, patterns, and line types) different from that of the contour surface F1B.

Figure 8A:
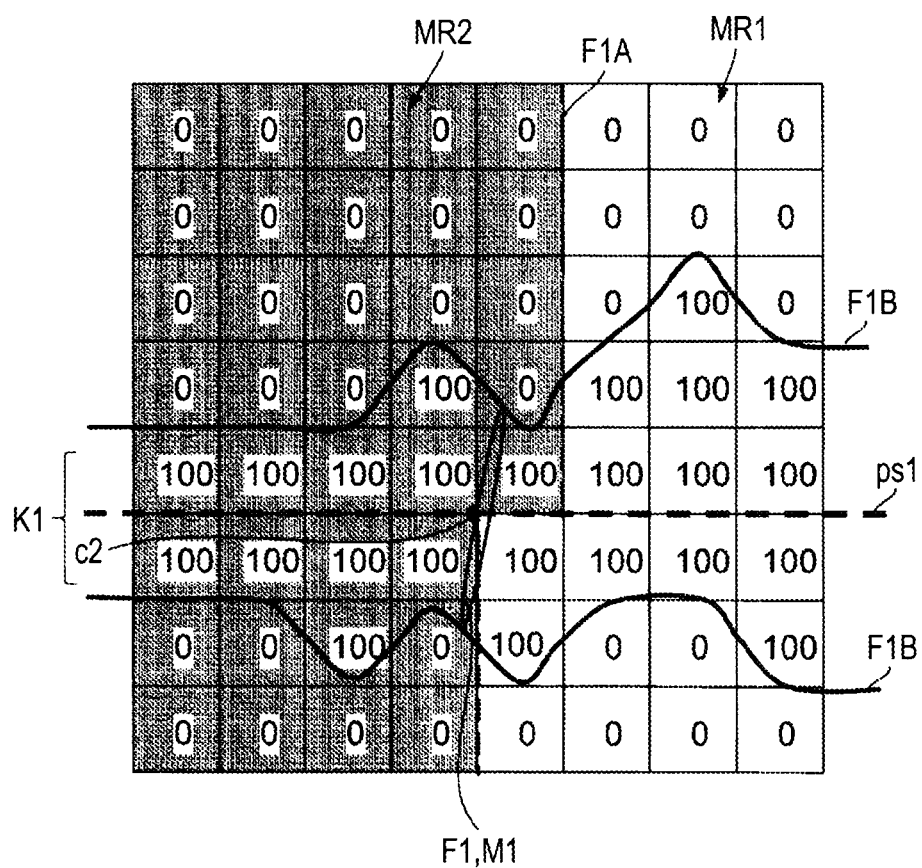
FIG. 8A is a diagram illustrating a third example of display of a highlighted cut surface of a blood vessel and each voxel value in a rendering image.

FIG. 8A is a diagram illustrating a third example of display of the highlighted cut surface F1 of the blood vessel K1 and each voxel value in a rendering image. The mask region MR1, the non-mask region MR2, and voxel values of voxels are shown in FIG. 8A in the same manner as in FIGS. 7A and 7B. In FIG. 8A, a central path ps1 of the blood vessel K1 is added thereto and highlighted. The region processing unit 161 may extract the region of the blood vessel K1 and calculate the central path ps1 of the blood vessel K1. The highlight information generator 163 generates a ring RG indicating a contour line of the cut surface F1 around an intersection point C2 between the central path ps1 and the mask boundary surface F1A. The display controller 164 superimposes the contour line highlight information M1 (for example, the ring RG) or the surface highlight information M2 on a rendering image for display. The ring RG is an example of the contour line highlight information M1.

Figure 8B:
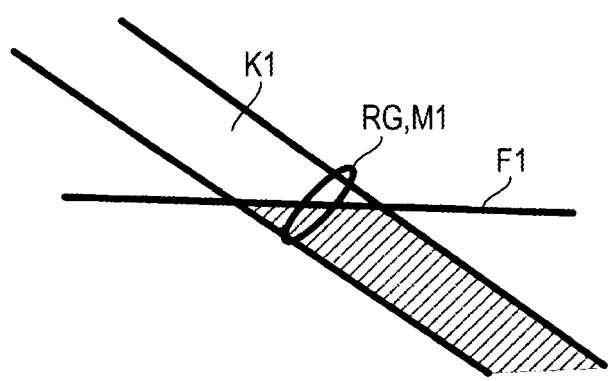
FIG. 8B is a diagram illustrating an example of display of a highlighted cut surface in a case where the cut surface is not perpendicular to a running direction of a blood vessel.

The direction of the ring RG can be adjusted. For example, the highlight information generator 163 may determine the direction of the ring RG based on the direction of the central path ps1 of the blood vessel K1. In this case, the direction of the ring RG may be determined based on voxel values of 64 voxels (4×4×4) around the intersection point C2. By adjusting the direction of the ring RG, it is possible to perform highlighted display using the contour line highlight information M1 or the surface highlight information M2 perpendicular to the running direction (direction in which the central path ps1 extends) of the blood vessel K1 using the ring RG in a state in which the cut surface F1 is not perpendicular to the running direction of the blood vessel K1 (refer to FIG. 8B). The surface highlight information M2 may perform highlighted display by displaying the inner surface of the ring RG in a display mode (for example, different colors, patterns, and line types) different from that of the contour surface F1B.

Figure 9:
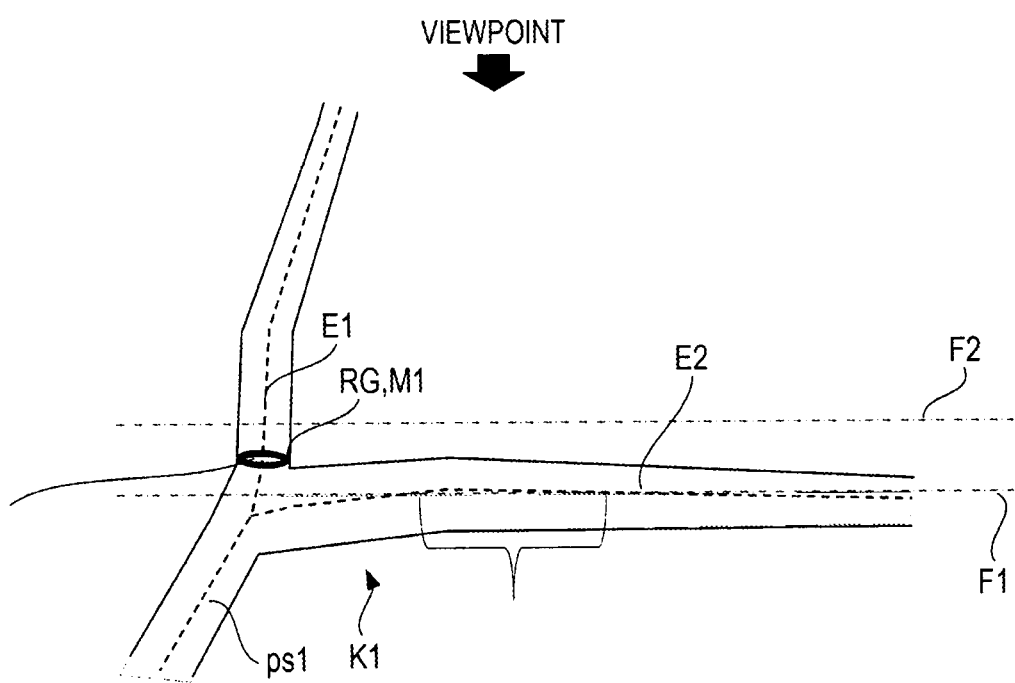
FIG. 9 is a diagram illustrating performing display of a highlighted cut surface while offsetting the display.

FIG. 9 is a diagram illustrating performing display of the highlighted cut surface F1 while offsetting the display. In FIG. 9, the blood vessel K1 is branched into a branch E1 and a branch E2. The cut surface F1 passes through both the branches E1 and E2 and is set along the branch E2. In this case, the display controller 164 may not display the ring RG in the branch E2 extending along the cut surface F1, but may display the ring RG in the branch E1 that does not extend along the cut surface F1. In this case, the display controller 164 may set an offset surface F2 which is offset from the cut surface F1. The offset surface F2 may or may not be parallel to the cut surface F1. The ring RG may be displayed on the contour line of the branch E1 of the blood vessel K1 which has passed through both the cut surface F1 and the offset surface F2. The position at which the ring RG is drawn may be a position passing through the offset surface F2 or a position different from that of the offset surface F2. The direction of the ring RG may or may not be parallel to the cut surface F1.

The offset between the cut surface F1 and the position where the ring RG is to be displayed can also be applied to the cases of FIGS. 7A, 7B, and 8A. For example, in FIGS. 7A, 7B, and 8A, it is assumed that the mask boundary surface F1A moves (offsets) along the blood vessel K1 in the horizontal direction of the drawing. In this case, the display controller 164 may display the ring RG at any position (for example, a position of the offset mask boundary surface) offset from the cut surface F1 regarding a blood vessel or a branch of a blood vessel which passes through both a non-offset mask boundary surface (the mask boundary surface corresponding to the cut surface F1) and the offset mask boundary surface.

The display controller 164 may analyze main components of a figure generated in the cross section at the cut surface F1 of the blood vessel K1. As a result of the analysis of the main components, the ring RG may be displayed in a case where the projected figure has a shape closer to a circle than that of a predetermined standard. The ring RG may not be displayed in a case where the projected figure has a flat shape rather than a shape closer to a circle than that of a predetermined standard. The highlighted display may be offset in the case where the projected figure has a flat shape rather than a shape closer to a circle than that of a predetermined standard.

Figure 10:
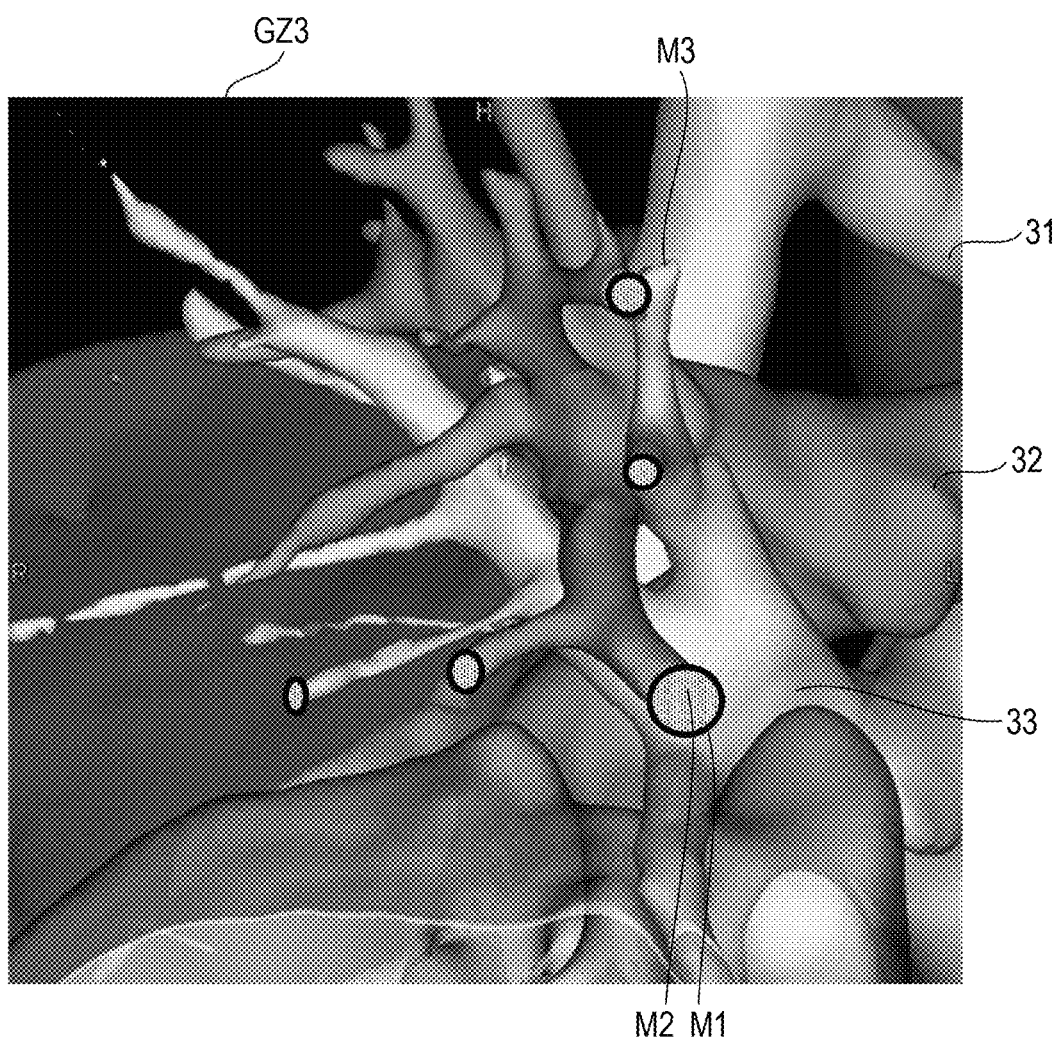
FIG. 10 is a diagram illustrating an example of display of highlighted cut surfaces in a surface rendering image.

FIG. 10 is a diagram illustrating an example of display of the highlighted cut surface F1 in a surface rendering image. A surface rendering image GZ3 including a bronchus 31, a pulmonary artery 32, and a pulmonary vein 33 is shown in FIG. 10. In FIG. 10, the cut surfaces F1 are set at the same position as ligation and separation points. The cut surfaces F1 are present in the pulmonary artery 32 and the pulmonary vein 33, and the contour line highlight information M1 and the surface highlight information M2 are displayed corresponding to the cut surfaces F1. An ended part M3 of the pulmonary vein 33 regardless of the cut surfaces F1 is reflected in FIG. 10. A user can grasp that the ended part M3 of the pulmonary vein 33 is so imaged (the pulmonary vein 33 is ended) because the ended part is not highlighted.

Figure 11:
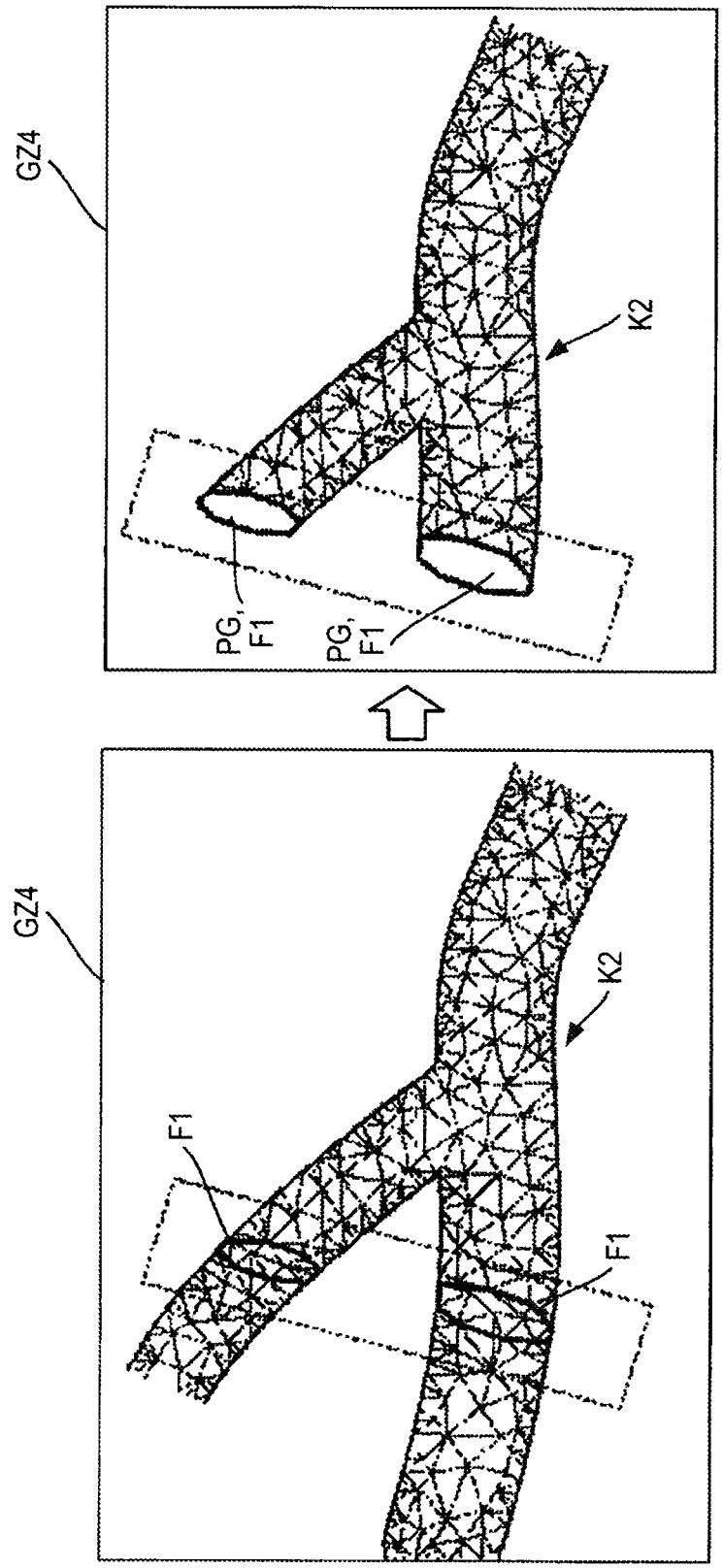
FIG. 11 is a diagram illustrating an example of a surface rendering image represented by a polygon mesh.

FIG. 11 is a diagram illustrating an example of a surface rendering image GZ4 represented by a polygon mesh. A blood vessel K2 represented by a polygon mesh is included in the surface rendering image GZ4. The blood vessel K2 has two branches which respectively have cut surfaces F1. In this case, the image generator 162 segments polygons along the cut surfaces F1 to form new polygons PG. Various kinds of image processing are performed using the surface rendering image GZ4 in consideration of the polygon mesh.

Figure 12:
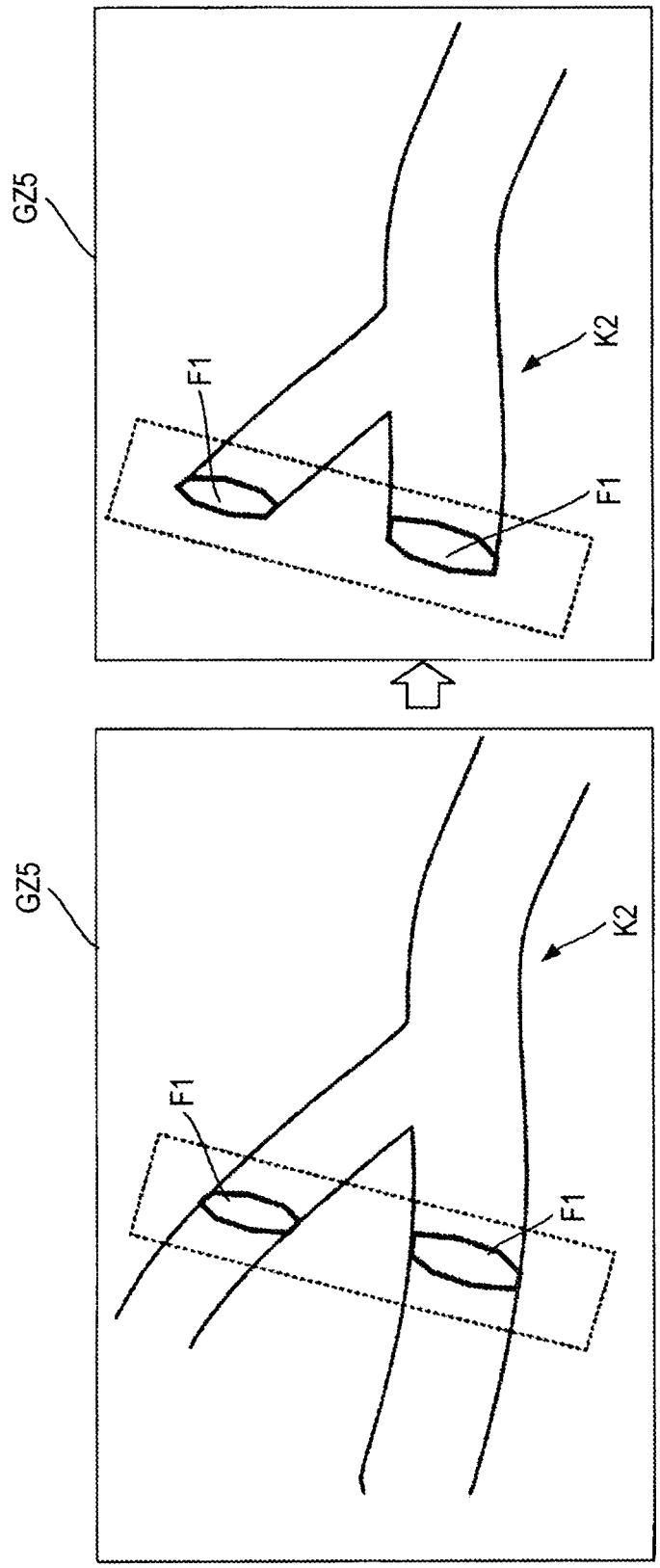
FIG. 12 is a diagram illustrating a display example of a surface rendering image shown in FIG. 11.

FIG. 12 is a diagram illustrating a display example of a surface rendering image GZ5 shown in FIG. 11. The wire frame of the polygon mesh is not usually drawn in the display of the surface rendering image GZ5. On the other hand, the display controller 164 only draws and displays the wire frames of the cut surfaces F1. Here, the wire frames of the cut surfaces F1 are set as the contour line highlight information M1. Accordingly, the contour line of the blood vessel K2 on the cut surfaces F1 is highlighted. The display controller 164 may display all the wire frames, and the contour lines of the wire frames of the cut surfaces F1 may be highlighted by changing the color or the thickness of the wire frames.

Figure 13:
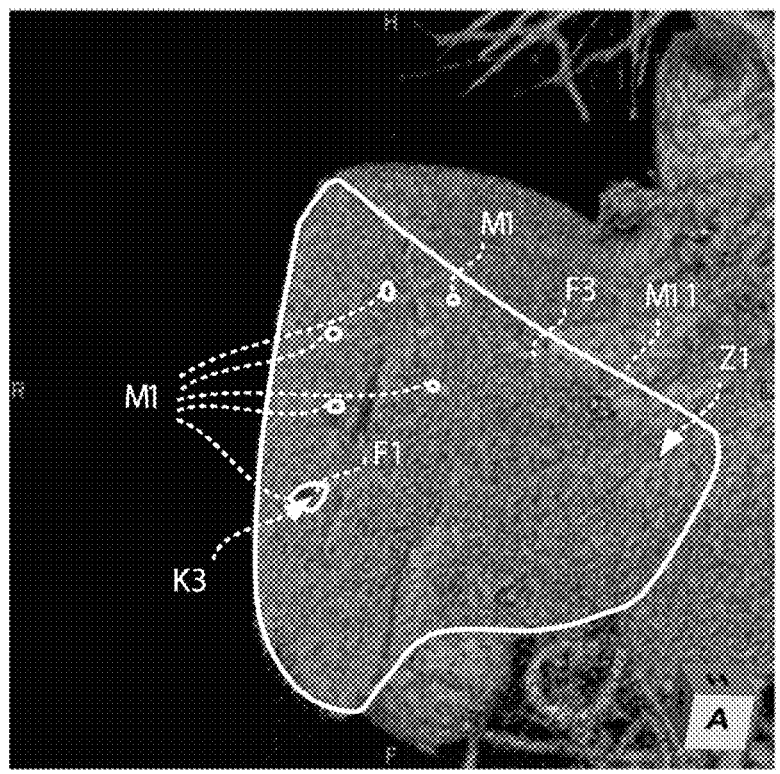
FIG. 13 is a diagram illustrating an example of display of highlighted cut surfaces of an organ to be cut.

FIG. 13 is a diagram illustrating an example of display of highlighted cut surfaces F3 of an organ Z1 to be cut. The highlight information generator 163 may generate highlight information for highlighting the organ Z1 itself on the cut surfaces F3. The highlight information includes at least contour line highlight information M11 in which a contour line of the organ Z1 on the cut surfaces F3 is highlighted. The highlight information may include surface highlight information M12 in which the inside surface of the contour lines of the cut surfaces F3 is highlighted. In FIG. 13, the contour line of the organ Z1 on the cut surfaces F3 and contour lines of one or more blood vessels K3 existing in the organ Z1 are highlighted using the contour line highlight information M1 and M11. In the raycast image, in some cases, it is difficult to grasp which portion of the organ Z1 is cut. In contrast, it is easy for a user to simultaneously grasp which portion of the organ Z1 is cut and which portion of a blood vessel in the organ Z1 is cut by highlighting the blood vessels K3 and the organ Z1 according to the cut surfaces F3. The contour line highlight information M11 may be displayed for the organ Z1 and the contour line highlight information M1 and the surface highlight information M2 may be displayed for the blood vessels K3. Accordingly, it is possible for a user to simultaneously grasp cut surfaces of an organ and points to be ligated and separated on the cut surfaces of an organ. In FIG. 13, the cut surfaces F1 according to the blood vessels K3 are included in the cut surfaces F3 according to the organ Z1.

In this manner, the medical image processing apparatus 100 can display highlighted points to be ligated and separated regarding blood vessels crossing the cut surfaces F1. Accordingly, a user easily grasps blood vessels to be ligated and separated while planning surgery. A user easily grasps blood vessels inside an organ which are usually difficult to grasp.

Even if a tissue is actually cut at the cut surface F1 using a mask, there is volume data of the tissue which has not been cut since the tissue has not yet cut at a point in time when the volume data is acquired. The display controller 164 can display the tissue so as to be cut by not displaying the non-mask region MR2. If masking is performed, it is difficult to determine whether there is the cut surface F1 on a mask boundary surface or a tissue is merely so imaged from the beginning. However, if the cut surface F1 is highlighted using highlight information such as a ring, it becomes clear that the position of the cut surface F1 is a ligation and separation point.

Up to here, although various embodiments have been described with reference to the accompanying drawings, it is needless to say that the present disclosure is not limited to such examples. It would be apparent for those skilled in the art that various modification examples or corrected examples are conceivable within the scope recited in the claims, and it would be understood that these fall within the technical scope of the present disclosure.

For example, a threshold value th2 (for example, a voxel value 50 for calculating the contour surface F1B) of voxel values for calculating a contour line of a blood vessel may not be coincident with a threshold value th3 (for example, a threshold value for making pixels used in ray-casting opaque or a threshold value for generating a surface through a marching cubes method or the like) for volume rendering.

The region processing unit 161 may not calculate a contour line of a blood vessel using the threshold value th2 by comparison with surrounding voxel values, but may simulate and calculate ray attenuation due to progression of a virtual ray and calculate a contour line of a blood vessel based on the ray attenuation. For example, the position at which initial ray attenuation is greater than or equal to a threshold value th4 when seen from a viewpoint side may be set to a surface (corresponding to a contour line) of a blood vessel. Each threshold value may be a fixed value or an adaptive value.

The cut surface F1 may be represented by a method other than masking using the region processing unit 161. For example, the cut surface setting unit 166 may set the cut surface F1 in a relative coordinate system with respect to volume data, limit voxels to those further on a back side than the cut surface F1 when seen from a viewpoint side, and generate volume rendering using voxel values of the voxels. In this case, if there are opaque voxels on the cut surface F1, these voxels are visualized. Accordingly, it is possible to visually recognize the cut surface F1 without using a mask.

The region processing unit 161 may generate masks representing the cut surfaces F1 based on the mask representing the shape of the organ Z1 and the masks representing the shapes of the blood vessels K1 to K3. The region processing unit 161 may generate highlight information based on an intersection of the surface of the mask representing the cut surfaces F1 and the surfaces of the mask representing the shape of the organ Z1 and the masks representing the shapes of the blood vessels K1 to K3. Accordingly, it is possible to flexibly visualize ligation and separation points according to how each mask region is generated in comparison with the case of highlighting cut surfaces based on an organ or blood vessels simply region-extracted as a single mask, for example. Respective offset distances may differ in contour lines generated for the organ Z1 and the blood vessels K1 to K3. As a result, it is possible to simulate a situation in which deviation occurs between the cut surfaces F1 of the organ and points of the blood vessels K1 to K3, included in the organ, to be ligated and separated. The blood vessels K1 to K3 are at least one of the blood vessels K1 to K3.

The cut surfaces F1 may not be cross sections for completely cutting an organ, but may be cross sections for cutting a part of an organ. Accordingly, it is possible to express a state in the middle of surgery by highlighting the cut surfaces F1. Even in a case where a cut is made while anticipating proliferation of hepatocytes, it is possible to apply display of the highlighted cut surfaces F1. In this case, the processing unit 160 may perform a deformation simulation by deforming the liver by pulling a piece of the liver after cutting a part of the liver, and highlight deformed cut surfaces F1.

The display of the highlighted cut surfaces F1 may be performed by being offset from the cut surfaces F1. The display controller 164 may highlight, for example, blood vessel paths or cut surfaces F1 using the ring RG or the like in front of a visual line direction. This is because actual ligation and separation points are positioned in front of a visual line direction of cut surfaces F1 or highlighted display is easily seen together with a rendering image during the highlighted display since the organ is incised in surgery and blood vessels are ligated and separated at an appropriate position on the blood vessels when the blood vessels are exposed.

The rendering image may include both an image portion obtained through volume rendering and an image portion obtained through surface rendering. For example, a contour line of an organ itself may be visualized through surface rendering and blood vessels may be visualized through volume rendering. For example, in a case of performing a simulation of segmentectomy of an organ, segments of the organ may be visualized through surface rendering and blood vessels may be visualized through volume rendering.

A subtype of a ray-casting method or a rendering method other than the ray-casting method may be included in the volume rendering. The volume rendering may be limited to rendering that causes ray attenuation (for example ray-casting method, ray-tracing method). The rendering may include stochastic raycast, cinematic volume rendering technique, ray tracing with respect to volume data, and the like. In a case of rendering in which a ray-casting method is combined with an MIP method, a tissue in which the cut surfaces F1 are highlighted may be visualized through the ray-casting method and other organs may be visualized through the MIP method. Accordingly, highlight information may be superimposed on the organ visualized through the MIP method. The rendering may include surface rendering. In the surface rendering, a surface to be rendered on the cut surface F1 may or may not be stretched.

The display controller 164 may not add highlight information to a rendering image after rendering, but may add highlight information thereto at a stage of rendering. For example, in a case of surface rendering, the image generator 162 may be set so as to perform rendering (contour line highlight rendering) for highlighting a contour line at a stage of rendering, to perform contour line highlight rendering. The highlighting of a contour line may include highlighting of a contour line of a tissue on a cut surface. This is not limited to the surface rendering. The same may apply to volume rendering.

The contour line may be at least a solid line, a dotted line, or a double line. A color may be set for the contour line. The contour line may be set according to the type of target organ. For example, arteries may be a red double line and veins may be a blue dotted line.

The medical image processing apparatus 100 may include at least the processor 140 and the memory 150. The port 110, the UI 120, and the display 130 may be externally attached to the medical image processing apparatus 100.

Volume data as a captured CT image which is transmitted from the CT scanner 200 to the medical image processing apparatus 100 is exemplified. Alternatively, the volume data may be stored by being transmitted to a server or the like (for example, image data server (PACS) (not shown)) on a network so as to be temporarily accumulated. In this case, the port 110 of the medical image processing apparatus 100 may acquire volume data from the server or the like when necessary via a wire circuit or a wireless circuit or may acquire volume data via any storage medium (not shown).

Volume data as a captured CT image which is transmitted from the CT scanner 200 to the medical image processing apparatus 100 via the port 110 is exemplified. It is assumed that this also includes a case where the CT scanner 200 and the medical image processing apparatus 100 are substantially combined as one product. This also includes a case where the medical image processing apparatus 100 is treated as a console of the CT scanner 200.

It has been exemplified that an image is captured by the CT scanner 200 to generate volume data including information on the inside of a subject. However, an image may be captured by other devices to generate volume data. Other devices include a magnetic resonance imaging (MRI) apparatus, a positron emission tomography (PET) device, an angiography device, or other modality devices. The PET device may be used in combination with other modality devices.

It can be expressed as a medical image processing method in which an operation of the medical image processing apparatus 100 is defined. It can be expressed as a program for causing a computer to execute each step of the medical image processing method.

Outline of Above Embodiment

One aspect of the above-described embodiment is a medical image processing apparatus 100 for visualizing a tissue and may include: an acquisition unit (for example, a port 110) having a function of acquiring volume data including the tissue; a cut surface setting unit 166 that sets a cut surface for cutting the tissue in the volume data; and a visualization processing unit 167 having a function of performing processing relating to visualization of the tissue. The visualization processing unit 167 may have a function of performing rendering that causes ray attenuation on the volume data to generate a rendering image including the tissue cut along the cut surface. The visualization processing unit 167 has a function of displaying display information including the rendering image, in which a contour line of the tubular tissue on the cut surface is highlighted, on a display unit (for example, a display 130).

Accordingly, in the medical image processing apparatus 100, it is possible to easily identify where the cut surface in the entire tissue is by checking highlighted display. In the highlighted display, for example, a branch of a blood vessel extends beyond a cut surface. However, it is possible to add a mark (an example of highlight information) which clearly indicates that a more distal side than the cut surface is excised. Even in a case where no mask is used, it is possible for a user to identify which position of a tissue is resected or excised by checking highlighted display. Even in a case where a mask is used, it is possible for a user to easily determine whether a more root side (non-terminal side) than the cut surface in a tissue is visualized or a contour surface of voxel values is visualized using the presence or absence of the highlighted display of a contour line on the cut surface. Accordingly, it is possible for a user to appropriately grasp points to be resected or excised, ligated, and separated in preoperative planning and intraoperative navigation.

The cut surface setting unit 166 may have a function of setting the cut surface F1 based on a mask boundary surface F1A which is a boundary between a mask region MR1 including voxels to be rendered among a plurality of voxels included in the volume data and a non-mask region MR2 including voxels not to be rendered. The visualization processing unit 167 may have a function of performing display by generating the rendering image based on voxel values of each of the voxels included in the mask region MR1 excluding voxel values of each of the voxels of the non-mask region MR2.

Accordingly, a tissue portion to be resected or excised on a more distal side than the cut surface is not displayed. Accordingly, a user can intuitively understand that the tissue is cut along the cut surface.

The tissue may be a tubular tissue (for example, a blood vessel K1). Accordingly, a user easily visually recognizes a resection point or an excision point of the tubular tissue that is often smaller than organs.

The tubular tissue may be included in an organ Z1. Accordingly, a user can visually recognize cut a point of the tubular tissue inside an organ which cannot be checked from the appearance.

The processing unit 160 may display a rendering image by indicating a direction of the tubular tissue. Accordingly, even in a case where, for example, the tubular tissue is cut obliquely against a path, a user can check resection points or excision points by adding the direction of the tubular tissue to easily resect or excise the actual tissue.

The visualization processing unit 167 may display the rendering image by offsetting a contour line of the tubular tissue on the cut surface F1 from the cut surface F1 for highlighting. Accordingly, in a case where the cut surface F1 set in the medical image processing apparatus 100 is different from a point that will actually be cut in surgery, the medical image processing apparatus 100 can clearly indicate highlight information in the point of a tissue corresponding to a resection point or an excision point, and it is possible to promptly set the cut surface F1 in the medical image processing apparatus 100. It is possible to simulate a situation in which deviation occurs between a cut surface F3 of an organ and a point of the tubular tissue, which is included in the organ, to be ligated and separated.

The tissue may be an organ. Accordingly, even in a case where it is difficult to grasp an organ in a rendering image, a contour line of the organ is clearly indicated. Therefore, a user can easily visually recognize the organ.

The visualization processing unit 167 may display the rendering image by highlighting a cut surface of an organ including the tubular tissue in addition to a cut surface of the tubular tissue. Accordingly, it is possible for a user to simultaneously grasp the cut surface F3 of the organ and a point to be ligated and separated on the cut surface F3 of the organ.

The visualization processing unit 167 may highlight the inside surface of the contour line on the cut surface and display the rendering image. Accordingly, a user easily appropriately grasps the cut surface of the tissue.

The rendering image may be a volume rendering image. In the volume rendering image, it is difficult to grasp a specific position in a three-dimensional space since the internal state of a tissue in the three-dimensional space is visualized on a two-dimensional plane. However, it is possible to easily visually recognize a resection point or an excision point through the above-described highlighted display.

One aspect of the above-described embodiment is a medical image processing method for visualizing a tissue, the method including steps of: acquiring volume data including the tissue; setting the cut surface F1 for cutting the tissue in the volume data; performing rendering that causes ray attenuation on the volume data to generate a rendering image including the tissue cut along the cut surface; and displaying display information including the rendering image, in which a contour line of the tissue on the cut surface is highlighted, on a display unit.

One aspect of the present embodiment may be a medical image processing program for causing a computer to execute the above-described medical image processing method.

The present disclosure is useful for a medical image processing apparatus which can easily visually recognize a tissue to be ligated, a medical image processing method, a medical image processing program, and the like.

What is claimed is:

1. A medical image processing apparatus for visualizing a tissue, comprising:
   a memory; and
   a processor configured to execute a process, the process comprising:
   acquiring volume data including the tissue;
   setting a cut surface for cutting the tissue in the volume data; and
   first performing processing relating to visualization of the tissue,
   wherein the first performing comprises:
   second performing rendering that causes ray attenuation on the volume data to generate a rendering image including the tissue cut along the cut surface; and
   displaying on a display unit display information including the rendering image in which a contour line of the tissue on the cut surface is highlighted.

2. The medical image processing apparatus according to claim 1, wherein
   the setting comprises setting the cut surface based on a mask boundary surface which is a boundary between a mask region including voxels to be rendered among a plurality of voxels included in the volume data and a non-mask region including voxels not to be rendered, and
   the first performing comprises displaying the rendering image generated based on voxel values that does not include voxel values of voxels of the non-mask region and that includes voxel values of voxels included in the mask region.

3. The medical image processing apparatus according to claim 1, wherein
   the tissue is a tubular tissue.

4. The medical image processing apparatus according to claim 3, wherein
   the tubular tissue is running through an organ.

5. The medical image processing apparatus according to claim 4, wherein
   the first performing comprises displaying on a display unit display information including the rendering image in which a contour line of the organ on the cut surface and a contour line of the tubular tissue on the cut surface are highlighted.

6. The medical image processing apparatus according to claim 3, wherein
   the first performing comprises displaying on the display unit display information including the rendering image in which a direction of the tubular tissue is indicated.

7. The medical image processing apparatus according to claim 3, wherein
   the first performing comprises displaying on the display unit display information including the rendering image in which a contour line of the tubular tissue on the cut surface is offset from the cut surface for highlighting.

8. The medical image processing apparatus according to claim 1, wherein
   the tissue is an organ.

9. The medical image processing apparatus according to according to claim 1, wherein
   the first performing comprises highlighting an inside surface of the contour line on the cut surface to display the rendering image.

10. The medical image processing apparatus according to claim 1, wherein
    the rendering image is a volume rendering image.

11. A medical image processing method for visualizing a tissue, the method comprising:
    acquiring volume data including the tissue;
    setting a cut surface for cutting the tissue in the volume data;
    performing rendering that causes ray attenuation on the volume data to generate a rendering image including the tissue cut along the cut surface; and
    displaying on a display unit display information including the rendering image in which a contour line of the tissue on the cut surface is highlighted.

12. A medical imaging system for visualizing a tissue, the medical imaging system comprising:
    a memory; and
    a processor configured to execute a process, the process comprising:
    acquiring volume data including the tissue from the CT scanner;
    setting a cut surface for cutting the tissue in the volume data; and
    first performing processing relating to visualization of the tissue,
    wherein the first performing comprises:
    second performing rendering that causes ray attenuation on the volume data to generate a rendering image including the tissue cut along the cut surface; and
    displaying on a display unit display information including the rendering image in which a contour line of the tissue on the cut surface is highlighted.

* * * * *